United States Patent [19]

Attig et al.

[11] Patent Number: 4,790,963

[45] Date of Patent: Dec. 13, 1988

[54] PROCESS FOR SYNTHESIS OF ESTERS FROM GASEOUS REACTANTS CONTAINING ORGANIC HYDROXY COMPOUNDS AND MIXTURES OF HYDROGEN AND CARBON MONOXIDE

[75] Inventors: Thomas G. Attig, Aurora; Anne M. Graham, Northfield Center; Frederick A. Pesa, Aurora, all of Ohio

[73] Assignee: The Standard Oil Company, Cleveland, Ohio

[21] Appl. No.: 642,406

[22] Filed: Aug. 20, 1984

[51] Int. Cl.$^4$ ............................................. C07C 67/36
[52] U.S. Cl. ..................... 260/410.9 R; 502/303; 502/304; 502/306; 502/313; 502/324; 502/326; 502/340; 502/345; 502/346; 518/713; 560/75; 560/86; 560/97; 560/100; 560/103; 560/105; 560/106; 560/114; 560/204; 560/232; 560/180; 560/182; 562/519
[58] Field of Search ............... 560/232, 114, 204, 97, 560/106, 100, 182, 75, 103, 86; 260/410.9 R; 518/713; 562/519

[56] References Cited

U.S. PATENT DOCUMENTS

| | | | |
|---|---|---|---|
| 3,193,584 | 7/1965 | Rylander et al. | 260/611 |
| 3,956,182 | 5/1976 | Ishimi | 562/535 |
| 3,998,876 | 12/1976 | Kato | 562/535 |
| 4,072,708 | 2/1978 | White et al. | 562/535 |
| 4,075,124 | 2/1978 | White et al. | 562/532 |
| 4,077,912 | 3/1978 | Dolhyj et al. | 252/461 |
| 4,085,065 | 4/1978 | White et al. | 562/535 |
| 4,235,798 | 11/1980 | Bartley et al. | 518/716 |
| 4,298,354 | 11/1981 | Hardman et al. | 44/56 |
| 4,309,314 | 1/1982 | Hargis et al. | 560/232 |
| 4,377,643 | 3/1983 | Pesa et al. | 518/713 |
| 4,478,955 | 10/1984 | Pesa et al. | 518/713 |

FOREIGN PATENT DOCUMENTS

| | | | |
|---|---|---|---|
| 30110 | 6/1981 | European Pat. Off. | 518/716 |
| WO81/00856 | 4/1981 | PCT Int'l Appl. | 560/232 |

Primary Examiner—Vivian Garner
Attorney, Agent, or Firm—Joseph G. Curatolo; Larry W. Evans

[57] ABSTRACT

A process for producing an ester is disclosed comprising contacting a gaseous reactant containing at least one organic hydroxy compound and a mixture of carbon monoxide and hydrogen with an ester synthesis catalyst of the formula $$M_a A_b Ru Cu_c N_z O_x$$

wherein
M is selected from the group consisting of Ce, Cr, Fe, Mn and mixtures thereof,
A is an alkali metal, alkaline earth metal or mixture thereof,
a is from 0 to about 1,
b is from 0.002 to about 10,
c is from 0.2 to about 20,
z is from 0 to about 196 by weight,
x is the number of oxygens needed to fulfill the valence requirements of the other elements.

The organic hydroxy compound can be provided separately or formed by contacting a mixture of carbon monoxide and hydrogen with an alcohol synthesis catalyst at an elevated temperature and pressure. The alcohol synthesis catalyst and ester synthesis catalyst can be in tandem or mixed.

22 Claims, No Drawings

PROCESS FOR SYNTHESIS OF ESTERS FROM GASEOUS REACTANTS CONTAINING ORGANIC HYDROXY COMPOUNDS AND MIXTURES OF HYDROGEN AND CARBON MONOXIDE

TECHNICAL FIELD

This invention relates to processes for the synthesis of esters from gaseous reactants containing organic hydroxy compounds and mixtures of hydrogen and carbon monoxide. More particularly, this invention relates to a process for synthesizing esters with a relatively high degree of selectivity from gaseous reactants containing at least one organic hydroxy compound and a mixture of hydrogen and carbon monoxide (e.g., synthesis gas) using a ruthenium-copper-containing catalytic complex.

BACKGROUND OF THE INVENTION

Esters are usually prepared by the reaction of alcohols or phenols with acids in the presence of a mineral acid catalyst.

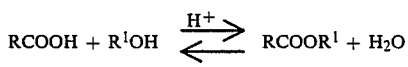

The reaction comes to equilibrium with appreciable amounts of the starting materials remaining. The equilibrium can be shifted to the right using a large excess of the alcohol. The water can be removed from the reaction by azeotropic distillation with a suitable solvent, such as benzene, thereby driving the reaction to completion.

There are a number of alternative methods for preparing esters, and each is useful under certain circumstances. The more useful of these methods are indicated below.

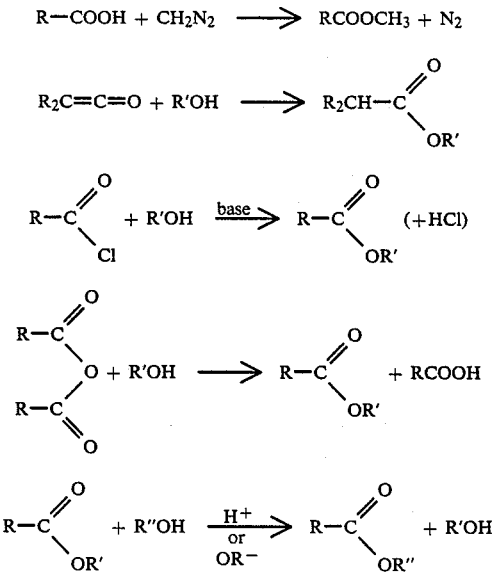

The reaction of an acid with diazomethane is hazardous except on a very small scale. Ketenes react with alcohols to give esters, but the reaction is of limited usefulness because of the limited availability of ketenes. The reaction of an acid chloride with an alcohol is usually used when it is desired to convert a valuable alcohol to an ester, usually the acetate. Most often the reaction is carried out in pyridine, which forms a salt with the HCl generated and prevents the solution from becoming acidic. An anhydride can be used in place of an acid chloride in a similar way. Transesterification is the reaction of an ester with an alcohol to yield a different ester. Transesterification is catalyzed by acids as well as bases.

In general, aliphatic and aromatic acids can be converted to esters by all of the methods referred to above. There are, however, limitations on the alcohols that are satisfactory in these reactions. Primary and secondary alcohols can generally be used in esterification of all kinds. Tertiary alcohols cannot be esterified in the presence of acids because they are easily converted to carbonium ions, which then undergo elimination or other reactions. Esterification of tertiary alcohols with acid chlorides can be effected under basic conditions.

Synthesis gas may be defined as any of several gaseous mixtures used for synthesizing a wide range of compounds, both organic and inorganic. Such mixtures result from reacting carbon-rich substances with steam (steam reforming) or steam and oxygen (partial oxidation). These mixtures contain chiefly carbon monoxide and hydrogen, and usually low percentages of carbon dioxide and nitrogen (less than 2%). The organic source materials may be natural gas, methane, naphtha, heavy petroleum oils or coke. The reactions are usually nickel-catalyzed steam-cracking (reforming) of methane or natural gas ($CH_4 + H_2O \rightarrow CO + 3H_2$); partial oxidation of methane, naphtha, or heavy oils; and the water-gas reaction with coke ($C + H_2O \rightarrow CO + H_2$).

Processes are known for converting synthesis gas to alcohols, aldehydes, acrylic acid, etc. These processes usually involve contacting synthesis gas with a transition-metal catalyst at elevated temperatures and pressures. For example, U.S. Pat. No. 4,298,354 discloses a process for converting synthesis gas to alcohols using an oxide-complex catalyst containing copper, thorium, an alkali metal and at least one other metal selected from the group consisting of Ca, Mo, Rh, Mn, Pt, Ce, Cr, Zn, Al, Ti, La, V, U, Ru, Re and Pd. U.S. Pat. No. 4,377,643 discloses the production of alkanes and oxygenated hydrocarbons, particularly alcohols, friom synthesis gas using a catalytic complex containing ruthenium, copper, an alkali metal and a promoter selected from the group consisting of Rh, Ir, Pd, and Pt.

SUMMARY OF THE INVENTION

The present invention contemplates the provision of a process for converting gaseous reactants containing at least one organic hydroxy compound and a mixture of hydrogen and carbon monoxide such as synthesis gas to esters with a relatively high degree of selectivity.

Broadly stated, the present invention provides a process for producing an ester or a mixture of esters comprising contacting a gaseous reactant containing at least one organic hydroxy compound and a mixture of carbon monoxide and hydrogen with an ester synthesis catalyst of the formula $$M_a A_b Ru Cu_c N_z O_x$$

wherein
  M is selected from the group consisting of Ce, Cr, Fe, Mn and mixtures thereof,
  A is an alkali metal, alkaline earth metal or mixtures thereof,
  a is from 0 to about 1, b is from 0.002 to about 10,
c is from 0.2 to about 20,
z is from 0 to about 1% by weight,
x is the number of oxygens needed to fulfill the valence requirements of the other elements.

The organic hydroxy compounds can be derived or provided separately and added to the carbon monoxide-hydrogen mixture prior to or at the time of contacting such mixture with the ester synthesis catalyst. The organic hydroxy compounds can also be derived from mixtures of carbon monoxide and hydrogen by contacting such mixtures with an alcohol synthesis catalyst at an elevated temperature and pressure and then adding such alcohol to the carbon monoxide-hydrogen mixture prior to or at the time of contacting such mixture with the ester synthesis catalyst. Alternatively, an alcohol synthesis catalyst can be intermixed with the ester synthesis catalyst, the desired ester being formed when the carbon monoxide-hydrogen mixture contacts this mixture of catalysts at an elevated temperature and pressure.

DESCRIPTION OF THE PREFERRED EMBODIMENTS

Ester Synthesis Catalyst

THe ester synthesis catalysts provided in accordance with the present invention are constituted of a ruthenium-copper-containing catalytic complex of the formula

$$M_aA_bRuCu_cN_zO_x$$

wherein
M is selected from the group consisting of Ce, Cr, Fe, Mn and mixtures thereof,
A is an alkali metal, alkaline earth metal or mixture thereof,
a is from 0 to about 1, preferably from about 0.1 to about 0.5;
b is from 0.002 to about 10, preferably from about 0.02 to about 6;
c is from 0.2 to about 20, preferably from about 0.4 to about 10;
z is from 0 to about 1%, preferably from about 0.5% to about 1% by weight;
x is the number of oxygens needed to fulfill the valence requirements of the other elements.

A can be selected from the group consisting of Na, Li, K, Rb, Cs, Be, Mg, Ca, Sr, Ba and mixtures thereof. A is preferably Na, Li, K, Rb, Cs, Mg or mixtures thereof.

The ester synthesis catalyst of the present invention is a mixed-metal oxide. In the process of the invention, this catalyst is preferably utilized in a partially reduced state. However, this catalyst is generally not totally reduced to elemental metal and thus retains an oxide character.

These ester synthesis catalysts may be prepared by conventional procedures known to those skilled in the art. Typically these procedures involve first mixing compounds containing the catalytic components in a liquid solution or slurry (e.g., a water solution or slurry), and heating. The catalyst precursor is recovered from the liquid then dried and calcined. Suitable compounds containing the catalytic components include but are not limited to oxides, hydroxides, inorganic salts (e.g., nitrates, phosphates, halides, carbonates, silicates, aluminates) and salts of organic acids (e.g., acetates, formates, butyrates, propionates, benzylates and the like).

Preferred ester synthesis catalysts of the invention containing the alkali metal component are prepared by recovering the catalyst precursor by adding to the aqueous solution of ruthenium, copper and "M" metal (if any) components, an alkali metal hydroxide to cause precipitation of the catalyst precursor, heating in the presence of the alkali metal, and thereafter filtering the precipitate.

These ester synthesis catalysts may be formed in any conventional manner, such as tabletting, pelleting, or supporting the active catalyst material on a carrier. The carrier is preferably inert and may include silica, alumina, Alundum, clay, alumina-silica, silicon carbide and the like.

A particularly useful coating procedure is disclosed in U.S. Pat. No. 4,077,912, which is incorporated herein by reference. Briefly, this method involves partially wetting the carrier, contacting the partially wetted carrier with a powdered precipitate of the catalytic components, then gently agitating the mixture until the catalytic complex is formed. Agitation is conveniently conducted by placing the partially wetted carrier in a rotating drum and adding the powdered precipitate until none is taken up by the carrier. The liquid used to wet the carrier may include inorganic or organic liquids and is dependent upon the type of catalytic components employed. The liquid and the catalytic components should have a relatively high degree of attraction for each other.

The catalytic components can also be impregnated on the carrier by depositing a solution containing the catalytic components on the carrier using known techniques, then drying and calcining.

The catalytic components may optionally be individually coated or impregnated on a carrier using the above-indicated techniques.

Procedures for the preparation of these catalysts are disclosed in copending U.S. application Ser. No. 552,556, filed Nov. 16, 1983, now U.S. Pat. No. 4,478,955, the disclosure of which is incorporated herein by reference.

Carbon Monoxide-Hydrogen Mixture

Although synthesis gas is preferred, any other gas composed primarily of hydrogen and carbon monoxide and having an $H_2/CO$ mole ratio of about 1:10 to 10:1, preferably about 1:3 to 3:1, can be employed. This mixture should contain as little sulfur as possible since sulfur is a known poison for copper containing catalysts. Preferably this mixture is essentially sulfur-free.

Organic Hydroxy Compound

One or more organic hydroxy compounds having up to about 10 carbon atoms and at least one hydroxy group can be employed. In a particularly advantageous embodiment these organic hydroxy compounds are monohydroxy compounds having from 1 to about 10, preferably from 1 to about 6 carbon atoms.

Monohydroxy compounds that are useful include methanol, ethanol, the propanols, butanols, pentanols, hexanols, heptanols, octanols, decanols, etc. Also useful as organic hydroxy compounds are the alicyclic analogs of the above-described alcohols; examples are cyclopentanol, cyclohexanol, cyclodecanol, etc.

Polyhydroxy compounds are also useful. These include ethylene, propylene, butylene, pentylene, hexylene and heptylene glycols wherein the hydroxy groups are separated by 2 carbon atoms; tri-, tetra-, penta-, hexa- and heptamethuylene glycols and hydrocarbon-substituted analogs thereof (e.g., 2-ethyl-1,3-trimethylene glycol, neopentyl glycol), as well as polyoxyalkylene compounds such as diethylene and higher polyethylene glycols, tripropylene glycol, dibutylene glycol, dipentylene glycol, and their monoethers.

Phenol, naphthols, substituted phenols (e.g., the cresols), and dihyroxyaromatic compounds (e.g., resorcinol, hydroquinone), as well as benzyl alcohol and similar dihydroxy compounds wherein the second hydroxy group is directly bonded to an aromatic carbon (e.g., 3-HOC$_6$H$_4$CH$_2$OH) are also useful, as are sugar alcohols of the general formula HOCH$_2$(CHOH)$_{1-5}$CH$_2$OH such as glycerol, sorbitol, mannitol, etc. (described in detail at pp. 569–588 of Vol. 2 of "Encyclopedia of Chemical Technology"), and their partially esterified derivatives, and methylol polyols such as pentaerythritol and its oligomers (di- and tripentaerythritol, etc.), trimethylolethane and trimethylolpropane.

An advantage of the process of the invention is that the organic hydroxy compounds used herein can be derived from the carbon monoxide-hydrogen mixtures of the invention by contacting such mixtures with a suitable alcohol synthesis catalyst at an elevated temperature and pressure to form the desired alcohol or mixture of alcohols. Since alcohol synthesis catalysts are available that operate at the same reaction conditions of temperature, pressure and space velocity as the ester synthesis catalysts of the invention, it is possible to operate the two catalysts (1) in tandem wherein the carbon monoxide-hydrogen mixture is first contacted with the alcohol synthesis catalyst to form an intermediate product containing alcohol, carbon monoxide and hydrogen, then the intermediate product is contacted with the ester synthesis catalyst to form the desired ester, or (2) to intermix the catalysts and contact the carbon monoxide-hydrogen mixture with the mixture of catalysts to form the desired ester.

Among the commercially available alcohol synthesis catalysts that can be used are the copper-zinc-aluminum and copper-chromate catalysts. These catalysts are well known to those skilled in the art. Three families of higher alcohol synthesis catalysts are preferred for use herein. The first is a copper-thorium containing complex of the formula $$Cu_fThD_gE_hO_y$$

wherein
D is one or more of Ca, Mo, Rh, Mn, Pt, Ce, Cr. Zn, Al, Ti, La, V, U, Re, Ru or Pd;
E is an alkali metal;
f is from about 0.5 to about 2.5, preferably from about 1.3 to about 1.7;
g is from about 0.01 to about 1, preferably from about 0.01 to about 0.6;
h is from about 0.05 to about 0.9, preferably from about 0.225 to about 0.55; and
y is a number such that the valence requirements of the other elements for oxygen is satisfied.

The alcohol synthesis catalysts in this family of catalysts can be used with or without an inert support. Useful supports include silica, alpha-alumina, Alundum, mullite and the like. These catalysts can be prepared by a procedure involving adding an alkali metal carbonate to an aqueous solution containing decomposable salts of thorium, copper and the "D" element, to form a precipitate, heating the precipitate in its mother liquor for a suitable time, neutralizing the precipitate, drying the precipitate and thereafter calcining and then reducing the precipitate. This procedure is described in detail in U.S. Pat. No. 4,298,354 which is incorporated herein by reference.

The second family of higher alcohol synthesis catalysts consists of ruthenium-copper-containing catalysts which have an active metal complex of the formula $$RuCu_jJ_kG_lN_mO_z$$

wherein
J is selected from the group consisting of Ce, Cr, Fe, Mn and mixtures thereof,
G is an alkali metal, alkaline earth metal or mixture thereof,
j is from about 0.2 to about 20, preferably from about 0.4 to about 10;
k is from 0 to about 1, preferably from about 0.1 to about 0.5;
l is from about 0.002 to about 10, preferably from about 0.02 to about 0.6;
m is from 0 to about 1%, preferably from about 0.5% to about 1% by weight;
z is the number of oxygens needed to fulfill the valence requirements of the other elements,
said active metal complex being supported by an activated carbon support having a surface area of at least about 300 square meters per gram, preferably about 300 to about 2500 square meters per gram, more preferably about 1050 to about 1250 square meters per gram. The weight ratio of the ruthenium-copper-containing active metal complex to the activated carbon support is in the range of about 30:70 to about 1:99, preferably about 10:90 to about 3:97, and advantageously about 5:95. G can be selected from the group consisting of Na, Li, K, Rb, Cs, Be, Mg, Ca, Sr, Ba and mixtures thereof. G is preferably Na, Li, K, Rb, Cs, Mg or mixtures thereof. Procedures for the preparation of these catalysts are disclosed in copending U.S. application Ser. No. 616,968, filed June 4, 1984, now U.S. Pat. No. 4,560,672, the disclosure of which is incorporated herein by reference.

The third family of higher alcohol synthesis catalysts consists of ruthenium-copper containing catalysts of the formula $$L_pRu_qCu_4Q_sN_tO_u$$

wherein
L is an alkali metal;
Q is Rh, Ir, Pd, Pt, or a mixture thereof;
p is about 0.002 to about 0.5;
q is about 0.5 to about 3;
r is about 0.5 to about 3;
s is about 0.5 to about 0.5;
t is from 0 to about 1% by weight; and
u is the number of oxygens needed to fulfill the valence requirements of the other elements.

Procedures for the preparation of this family of catalysts are disclosed in U.S. Pat. No. 4,377,643, which is incorporated herein by reference.

PROCESS

The inventive process can be carried out by contacting in vapor or gaseous phase the organic hydroxy compound and carbon monoxide-hydrogen mixture with the above-described ester synthesis catalyst in a suitable reactor. Alternatively, the carbon monoxide-hydrogen mixture is first contacted with an alcohol synthesis catalyst at an elevated temperature and pressure to form an intermediate product containing at least one desired organic hydroxy compound, hydrogen and carbon monoxide, and then the intermediate product is contacted with the ester synthesis catalyst of the invention at an elevated temperature and pressure to form the desired ester or mixture of esters. Advantageously the same temperature, pressure and space velocity are employed in the formation of both the intermediate and final products. The molar ratio of carbon monoxide to organic hydroxy compound is in the range of about 20:1 to about 1:10, preferably about 10:1 to about 1:5.

In still another embodiment the ester synthesis catalyst and alcohol synthesis catalyst are intermixed and contacted with the carbon monoxide-hydrogen mixture at an elevated temperature and pressure to form the desired ester or mixture of esters. The weight ratio of alcohol synthesis catalyst to ester synthesis catalyst is dependent upon the relative activity level of each catalyst but is generally in the range of about 1:20 to about 1:1. In general smaller amounts of methanol synthesis catalysts are required than higher alcohol synthesis catalysts due to the fact that the methanol synthesis catalysts tend to be more active.

The reaction can be carried out in either a fluidized-bed mode or fixed-bed mode, continuously or in batch operation. Preferably, when the carbon monoxide-hydrogen mixture is contacted with the alcohol synthesis catalyst first then followed by contacting the resulting intermediate product with the ester synthesis catalyst, both catalyst beds are operated in the same manner (i.e. fluidized or fixed) and on a continuous basis.

The space velocity of the gaseous reactants (i.e., carbon monoxide-hydrogen mixture/organic hydroxy compound, carbon-monoxide hydrogen mixture/intermediate product, or carbon monoxide-hydrogen mixture) is not critical but should be about 100 to about 10,000, preferably about 500 to about 5000 liters of reactant per liter of catalyst per hour.

The reaction pressure should normally be from about 500 to about 5000 psi and is preferably from about 500 to about 2000 psi. Although there is no real upper limit to the reaction pressure, pressures higher than about 2000 psi are normally not employed because of the high expense involved. Also, pressures as low as about 250 psi can be employed, although it is preferable to operate at at least about 500 psi because the formation of esters is favored at higher pressures.

The reaction temperature should be maintained between about 250° C. and about 400° C., preferably from about 250° C. to about 350° C.

The contact time of reactant with catalyst is generally between about 10 seconds and about 200 seconds, preferably between about 15 seconds and about 140 seconds.

PRODUCT

The products produced by the process of the invention are constituted primarily of esters, alkanes and olefins. The esters can be characterized by the formula RCOOR' wherein R is a hydrocarbon group of from 1 to about 30 carbon atoms and R' is a hydrocarbon group of from 1 to about 10 carbon atoms. The alkanes include methane and the gaseous alkanes having more than one carbon atom. The olefins include those olefins having more than 2 carbon atoms. Esters as well as alcohols and aldehydes having from one to about 5 carbon atoms are usually present in an aqueous product phase. Esters as well as olefins, paraffins, carboxylic acids, aldehydes and alcohols are usually present in an organic or oil product phase.

These products are useful as additives for diesel fuels, synthetic lubricants and plastics. Where conversion is maintained at a moderate or low level, these products can be recovered from the reactor effluent, and the remaining synthesis gas recycled to the reaction.

One of the advantages of the inventive process is that the selectivity to the formation of esters is relatively high.

In order to further illustrate the process of the present invention, the following example is provided. Unless otherwise indicated, all parts and percentages are by weight.

EXAMPLE

Part A

A catalyst of the formula 5% $Na_{0.3}RuCuO_x$/95% Alundum was prepared according to the following procedure. An amount of ruthenium chloride and copper chloride required to give 0.03 moles of each metal was dissolved in 250 milliliters of water with stirring for 30 minutes. Aqueous sodium hydroxide (50% by weight) was added dropwise, with stirring, until the pH reached and remained at 8.3 to 8.5. The resulting slurry was heated near boiling for 30 minutes with constant stirring, then cooled. The pH was adjusted to 7.5. The mixture was filtered, washed, and reslurried with subsequent filtering and washing steps until the molar ratio of ruthenium to sodium present was 0.3. The solid mixed oxide was dried at 125° C. for about 16 hours, then calcined for three hours at about 350° C. (in air) and ground to pass 140 mesh (0.105 millimeters).

The catalyst was coated upon an alumina-silica support in the following manner. 25 grams of Norton SA 5223 Alundum, 10/30 mesh (0.595 millimeters-2.00 millimeters) were placed in a vessel. 1.25 grams distilled water were sprayed onto the Alundum which was rolled for approximately 10 minutes and the procedure was repeated. The metal oxide catalyst, in an amount calculated to give a total of 0.015 moles of active metal, was added in two equal portions with 15 minutes rolling after each. The coated catalyst was dried for about 16 hours at 125° C. and calcined for three hours at 350° C.

The catalyst was partially reduced in the following manner. A 20 cc stainless steel tube reactor was packed with catalyst, and hydrogen gas was introduced into the reactor at 150–200 cc/min. at atmospheric pressure. An electric block furnace which was placed around the reactor was increased in 50° C. increments stepwise until 500° C. was reached. The final temperature was maintained for two hours, at which time the reactor was allowed to cool with hydrogen flow being continued. The catalyst was nitrided after reduction by contacting the catalyst with ammonia for several hours at atmospheric pressure and a temperature of about 400° C., and then cooling under ammonia.

Part B

Following catalyst reduction and subsequent cooling to room temperature, the reactor from Part A containing the catalyst from Part A was charged to a pressure of 1300 PSIG with hydrogen. The split block electric furnace surrounding the reactor was activated and set for the run temperature of 350° C. The system was allowed to equilibrate for at least 15 minutes at run temperature in flowing hydrogen at a rate of 150 cm³/min. before carbon monoxide and methanol flows were started and adjusted to the desired flow rates. The carbon monoxide to hydrogen to methanol mole ratio was 3:7:0.5. The space velocity was 3300 liters of reactant per liter of catalyst per hour. After about one to one and one-half hours of reaction, the off-gas (effluent) was sampled and analyzed and the condensible product diverted from a pre-run receiver to a product collection receiver. A recovery run proceeded for one and one-half hours during which time the off-gas was analyzed by gas chromatography and its volume measured. The liquid product also was weighed and analyzed.

In addition to gas chromatography analysis for the gas phase, hydrocarbons having more than three carbon atoms were determined by flame ionization detection. Liquid phase hydrocarbons and oxygenated hydrocarbons were analyzed by gas chromatography. The results reported in the Tables below were calculated as follows:

Selectivity =

$$\frac{\text{Moles Product} \times \text{number of carbon atoms in product}}{\text{Moles CO input} - \text{Moles CO effluent}} \times 100$$

CO Conversion =

$$\frac{\text{Moles of CO input} - \text{moles CO effluent}}{\text{Moles of CO input}} \times 100$$

Selectivity to gas and aqueous phase products are reported as a weight percent of total products. Selectivity to oil phase products are reported as a weight percent of total oil phase product obtained, calculated as above. Weight percent hydrocarbons are reported as weight percent of total product weight. Carbon dioxide, methanol and water were not considered in the calculations.

TABLE I

| Component | Weight Percent |
|---|---|
| Esters | 16.5 |
| Methane | 14.0 |
| Ethane | 2.9 |
| Propane | 3.1 |
| Butane | 1.9 |
| Ethylene | 2.9 |
| Propylene | 6.6 |
| Butylene | 3.5 |
| Ethanol | 1.6 |
| Propanol | 1.0 |
| Butanol | 1.4 |
| Pentanol | 1.0 |
| Acetic Acid | 2.7 |
| Propionic Acid | 1.0 |
| Butyric Acid | 0.8 |
| Valeric Acid | 0.6 |
| Higher Alkanes | 15.5 |
| Higher Olefins | 18.0 |
| Higher Alcohols | 0.1 |
| Higher Carboxylic Acids | 4.0 |
| Aldehydes | 0.8 |

TABLE II

| Component | Selectivity |
|---|---|
| Esters | 16.6 |
| Alkanes | 37.3 |
| Olefins | 31.0 |
| Alcohols | 5.3 |
| Acids | 9.0 |
| Aldehydes | 0.8 |

The CO conversion was 80%. Selectivity of acids to the aqueous phase was 5.2%, and to the oil phase was 4.0%. Selectivity of esters to the oil phase was 16.6%.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process for producing an ester comprising contacting a gaseous reactant containing at least one organic hydroxy compound and a mixture of carbon monoxide and hydrogen with an ester synthesis catalyst of the formula $$M_a A_b Ru Cu_c N_z O_x$$

wherein
M is selected from the group consisting of Ce, Cr, Fe, Mn and mixtures thereof,
A is an alkali metal, alkaline earth metal or mixture thereof,
a is from 0 to about 1,
b is from 0.002 to about 10,
c is from 0.2 to about 20,
z is from 0 to about 1% by weight, and
x is the number of oxygens needed to fulfill the valence requirements of the other elements.

2. The process of claim 1 wherein said organic hydroxy compound is made by contacting said mixture of carbon monoxide and hydrogen with an alcohol synthesis catalyst.

3. The process of claim 2 wherein said ester synthesis catalyst and said alcohol synthesis catalyst are intermixed with each other.

4. The process of claim 3 wherein the ratio of said alcohol synthesis catalyst to said ester synthesis catalyst is in the range of about 1:20 to about 1:1.

5. The process of claim 2 wherein said mixture of carbon monoxide and hydrogen initially contacts said alcohol synthesis catalyst to form an intermediate product, said intermediate product then contacts said ester synthesis catalyst to form said ester.

6. The process of claim 2 wherein said alcohol synthesis catalyst is a copper-thorium-containing complex of the formula $$Cu_f Th D_g E_h O_y$$

wherein
D is one or more of Ca, Mo, Rh, Mn, Pt, Ce, Cr, Zn, Al, Ti, La, V, U, Re, Ru or Pd;
E is an alkali metal;
f is from about 0.5 to about 2.5;
g is from about 0.01 to about 1;
h is about 0.05 to about 0.9; and
y is a number such that the valence requirements of the other elements for oxygen is satisfied.

7. The process of claim 6 wherein said copper-thorium-containing complex is supported on an inert support.

8. The process of claim 2 wherein said alcohol synthesis catalyst has an active metal complex of the formula $$RuCu_jJ_kG_lN_mO_z$$

wherein

J is selected from the group consisting of Ce, Cr, Fe, Mn and mixtures thereof,

G is an alkali metal, alkaline earth metal or mixture thereof, j is from about 0.2 to about 20;

k is from 0 to about 1;

l is from about 0.002 to about 10;

m is from 0 to about 1% by weight;

z is the number of oxygens needed to fulfill the valence requirements of the other elements, said active metal complex being supported by an activated carbon support having a surface area of at least about 300 square meters per gram.

9. The process of claim 2 wherein said alcohol synthesis catalyst is a ruthenium-copper containing catalyst of the formula $$L_pRu_qCu_rQ_sN_tO_u$$

wherein

L is an alkali metal;

Q is Rh, Ir, Pd, Pt, or a mixture thereof;

p is about 0.002 to about 0.5;

q is about 0.5 to about 3;

r is about 0.5 to about 3;

s is about 0.5 to about 0.5;

t is from 0 to about 1% by weight; and u is the number of oxygens needed to fulfill the valence requirements of the other elements.

10. The process of claim 1 wherein the mole ratio of hydrogen to carbon monoxide is from about 1:10 to about 10:1.

11. The process of claim 1 wherein the mole ratio of carbon monoxide to organic hydroxy compound is about 20:1 to about 1:10.

12. The process of claim 1 wherein said mixture of carbon monoxide and hydrogen is synthesis gas.

13. The process of claim 1 wherein said gaseous reactant is at a pressure of about 500 psi to about 5000 psi.

14. The process of claim 1 wherein said gaseous reactant is at a temperature of about 250° C. to about 400° C.

15. The process of claim 1 wherein the space velocity for said gaseous reactant is from about 100 to about 10,000 liters of gaseous reactant per liter of catalyst per hour.

16. The process of claim 1 wherein said organic hydroxy compound has up to about 10 carbon atoms and at least one hydroxy group.

17. The process of claim 1 wherein said organic hydroxy compound is a monohydroxy compound having from 1 to about 10 carbon atoms.

18. The process of claim 1 wherein A is selected from the group consisting of Na, Li, K, Rb, Cs, Mg or mixtures thereof.

19. The process of claim 1 wherein a is is from about 0.1 to about 0.5.

20. The process of claim 1 wherein b is from about 0.02 to about 6.

21. The process of claim 1 wherein c is from about 0.4 to about 10.

22. The process of claim 1 wherein said ester synthesis catalyst is partially reduced.

* * * * *